United States Patent [19]

Yagawara et al.

[11] Patent Number: 5,012,671
[45] Date of Patent: May 7, 1991

[54] GAS DETECTING DEVICE

[75] Inventors: Shinji Yagawara; Wasaburo Ohta, both of Yokohama, Japan

[73] Assignee: Ricoh Company, Ltd., Tokyo, Japan

[21] Appl. No.: 434,255

[22] Filed: Nov. 13, 1989

[30] Foreign Application Priority Data

Nov. 15, 1988 [JP] Japan .................... 63-289880
Nov. 16, 1988 [JP] Japan .................... 63-290974

[51] Int. Cl.$^5$ ............................ G01N 27/12
[52] U.S. Cl. .................... 73/31.06; 422/98
[58] Field of Search ............ 73/31.06; 338/34; 422/98

[56] References Cited

U.S. PATENT DOCUMENTS 4,580,439 4/1986 Manaka .................... 73/31.06
4,792,433 12/1988 Katsura et al. ............ 73/31.06 X

FOREIGN PATENT DOCUMENTS 9995 1/1979 Japan .................... 422/98
9996 1/1979 Japan .................... 422/98
166032 12/1980 Japan .................... 422/98

Primary Examiner—Hezron E. Williams
Assistant Examiner—Joseph W. Roskos
Attorney, Agent, or Firm—Oblon, Spivak, McClelland, Maier & Neustadt

[57] ABSTRACT

A gas detecting device includes a substrate and a plurality of overhang portions made from an electric insulation material and disposed in a space over the substrate. A gas sensitive film is made from a metallic oxide semiconductor material and is mounted on each of the overhang portions. A pair of detecting leads is connected to the gas sensitive film. A heater lead for heating the gas sensitive film is mounted on each of the overhang portions. The gas sensitive film of at least one of the plurality of overhang portions has a composition ratio of metal to oxygen different from that of the other gas sensitive films whereby a specified gas can be selectively detected on the basis of the response of the plurality of metallic oxide semiconductors to the gas.

22 Claims, 6 Drawing Sheets

GAS DETECTING DEVICE

BACKGROUND OF THE INVENTION

The present invention relates to a gas detecting device for detecting a gas in an atmosphere. More particularly, the invention relates to a gas detecting device which is suitable for using as a gas alarm for leak of a city gas or a liquefied petroleum (LP) gas.

The present invention also relates to a gas detecting device which discriminates a gas from an atmosphere including a plurality of different kind of gases.

Generally, a gas detecting device is responsive to various kind of gases such as isobutane, propane, ethane, methane, ethanol, propylene, toluene, xylene, methanol, hydrogen, carbon monoxide, etc. Therefore, when a specified gas is to be detected, the gas detecting device generates a noise signal in response to another gas mixed in the atmosphere. For example, with regard to a household gas detector (gas alarm), it is desirable that the detector is sensitive only to a methane gas when a city gas is used. However, the gas detector which is usually disposed on a ceiling is sensitive to the water vapor or an alcohol gas which is often generated in a domestic kitchen.

Therefore, in order to selectively detect a specified gas, the conventional gas detecting device is constructed in such a way that it comprises a filter means for selecting the specified gas or that the functional temperature thereof is arranged so that the detector becomes most sensitive to the specified gas. However, such a way for selectively detecting a gas is undesirable from an aspect of cost as well as reliability of detection of the specified gas.

There are two types of the gas detecting device. One is a semiconductor detection type using a metallic oxide and the other is a contact combustion type using a catalyst. Either of the two types has to heat a gas sensitive element by using a heater means, which consumes a relatively large power. Besides, the conventional gas decting device is not fully and accurately responsive to the gas.

In order to save the power consumption and improve the responsiveness of the detector, a gas detecting device is proposed in Japanese Patent Application Laying Open (KOKAI) No. 61-191953 wherein a minutely processed fine microheater of Japanese Patent Publication (KOKOKU) No. 62-2438 is used. The proposed gas detector is improved in the points of power consumption and responsiveness to the gas. However, the proposed gas detector is economically still undesirable since it requires a filter to select a gas. Also, the filter is for selecting one specified gas from a mixed gas atmosphere excluding other gases. Therefore, the conventional gas detector using the filter is not capable of discriminating a plurality of gases by itself.

SUMMARY OF THE INVENTION

It is therefore an object of the present invention to provide a gas detecting device which is capable of detecting a specified gas or discriminating a plurality of gases without using a filter means as in the prior art.

The object of the invention can be achieved by a gas detecting device comprising: a substrate; a plurality of overhang members made from a dielectric material and disposed in a space above the substrate; a gas sensitive member made from a metallic oxide semiconductor mounted on each of the overhang members; a pair of detecting leads connected to the gas sensitive member; a heater means disposed on each of the overhang members, wherein at least one gas sensitive member mounted on one of the overhang members has a metal oxygen composition ratio different from that of the other gas sensitive members.

More particularly, the gas detecting device in accordance with the present invention comprises: a substrate; an overhang member made from a dielectric material and disposed in a space above the substrate; at least a pair of detecting leads separated from each other by a predetermined distance and disposed in a detecting area arranged on the overhang member; at least one heater lead disposed on the overhang member substantially parallel with the detecting leads; and a gas sensitive layer disposed in the detecting area in contact with the pair of detecting leads, in which a gas is detected by measuring the resistance of the gas sensitive layer which reacts upon the gas and changes the resistance thereof, wherein the gas detecting device is characterized in that two or more overhang members each having the heater lead, the detecting leads and the gas sensitive layer mounted thereon are disposed on the substrate and that at least one of the gas sensitive layers comprises a metallic oxide semiconductor having a metal oxygen composition ratio different from that of the other gas sensitive layers so as to selectively detect the gas.

It is to be remarked that the inventors of this application confirmed that a gas can be selectively detected by an arrangement in which the gas detecting device comprises a plurality of microheaters and gas sensitive films and in which the plurality of gas sensitive films composed of a metallic oxide semiconductor film have a metal oxygen composition ratio different from each other. The present invention was made on the basis of this confirmed principle.

In accordance with the present invention, the gas detecting device comprises at least two gas sensitive layers each composed of a metallic oxide semiconductor film having a different composition ratio between metal and oxygen from that of the other metallic oxide semiconductor films so that a gas can be discriminated from the detection result of the plurality of gas sensitive layers.

An advantage of the above-mentioned gas detecting device in accordance with the present invention is that a predetermined specified gas can be easily and reliably detected only by changing the composition ratio between metal and oxygen of each of the plurality of gas sensitive layers.

The above-mentioned object of the present invention can also be achieved by a gas detecting device comprising: a substrate; an overhang member made from an electric insulation material and disposed in a space above the substrate; a metallic oxide semiconductor layer for detecting a gas disposed on the overhang member; an electrode lead connected to the metallic oxide semiconductor layer; and a heater lead disposed substantially in parallel with the electrode lead, wherein a plurality of the overhang members each having the metallic oxide semiconductor layer, the electrode lead and the heater lead mounted thereon are disposed on the substrate and wherein at least one overhang member has a different metallic oxide semiconductor layer material and a different electrode lead material from those of the other overhang members so that a plurality kinds of gas can be discriminated.

The above-mentioned gas detecting device in accordance with the present invention comprises a plurality of microheaters and gas detection elements, each element composed of a metallic oxide semiconductor film to which an electrode lead is connected, wherein at least one metallic oxide semiconductor film is made from a material different from that of the other metallic oxide semiconductor films and at least one electrode lead is made from a material different from that of the other electrode leads so that a plurality of kinds of gas can be discriminated by one gas detecting device.

An advantage of the above-mentioned gas detecting device in accordance with the present invention is that a plurality of kinds of gas can be easily and reliably discriminated without using a filter means.

Further objects and advantages of the present invention will be apparent from the following description of the preferred embodiments of the invention as illustrated in the accompanying drawings.

DESCRIPTION OF THE PREFERRED EMBODIMENTS

Figure 1:
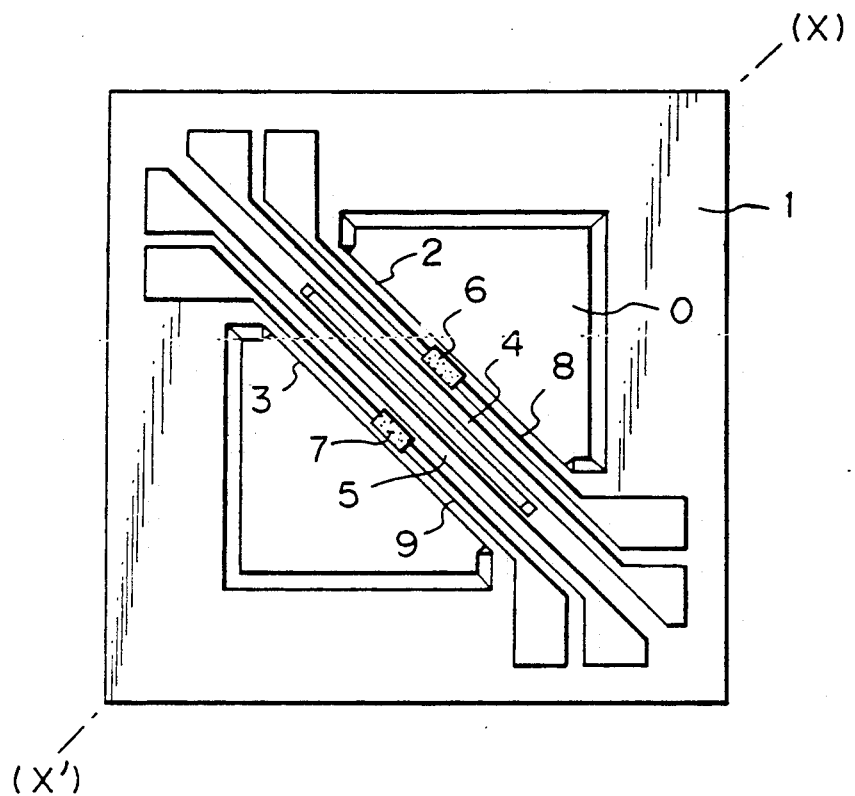
FIG. 1 is a plan view of an example of a gas detecting device in accordance with the present invention.
Figure 2:
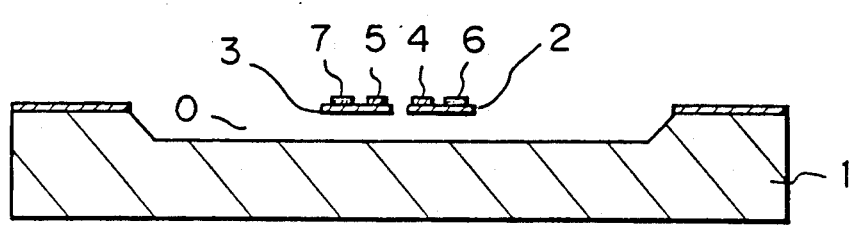
FIG. 2 is a sectional view of the gas detecting device of FIG. 1 taken along the line X—X' in FIG. 1.

FIGS. 1 and 2 represent an embodiment of the gas detecting device in accordance with the present invention which has a bridge-like structure.

This embodiment comprises a substantially square shaped substrate 1 having a substantially square shaped recess 0 undercut by etching in the central portion thereof. Two overhang portions 2 and 3 are disposed over the recess 0. The overhang portions are made from an electric insulation material. The two overhang portions 2 and 3 are disposed side by side along the diagonal of the recess 0 in a space above the recess 0, each portion being supported at both ends thereof by the edge of the recess 0, forming a bridge-like structure.

The substrate 1 is made from a material which is not deformed at a high temperature and can easily undercut by etching. Examples of such a material are silicon (Si), aluminium (Al), copper (Cu), nickel (Ni), chromium (Cr), etc. It is desirable to use Si (100) of the above-mentioned examples as the substrate material since the surface (100) of the material is adequate to be etched with the use of a known anisotropy etching solution. Preferably, the substrate 1 has a size of 1 to 4 mm square and 0.1 to 1 mm thick.

The two overhang portions 2 and 3 are formed by etching the substrate 1 to undercut it. On each of the overhang portions 2 and 3 are disposed a heater lead 4, 5, a metallic oxide semiconductor film 6, 7 and a detecting lead 8, 9. The metallic oxide semiconductor film 6, 7 each is arranged as a gas sensitive layer to which the detecting lead 8, 9 is connected to detect the gas. It is preferable to use platinum (Pt) or gold (Au) as a material for the heater leads 4 and 5 and the detecting leads 8 and 9.

As mentioned before, the metallic oxide semiconductor films 6 and 7 mounted on the overhang portions 2 and 3, respectively, are formed from the same metallic oxide which however has a different composition ratio of metal to oxygen changed for each of the metallic oxide semiconductor films 6 and 7, respectively. Examples of metal for composing the metallic oxide are tin, zinc, iron, titanium, indium, nickel, tungsten, cadmium, etc. It is most preferable to use tin of all the examples mentioned above.

Figure 3:
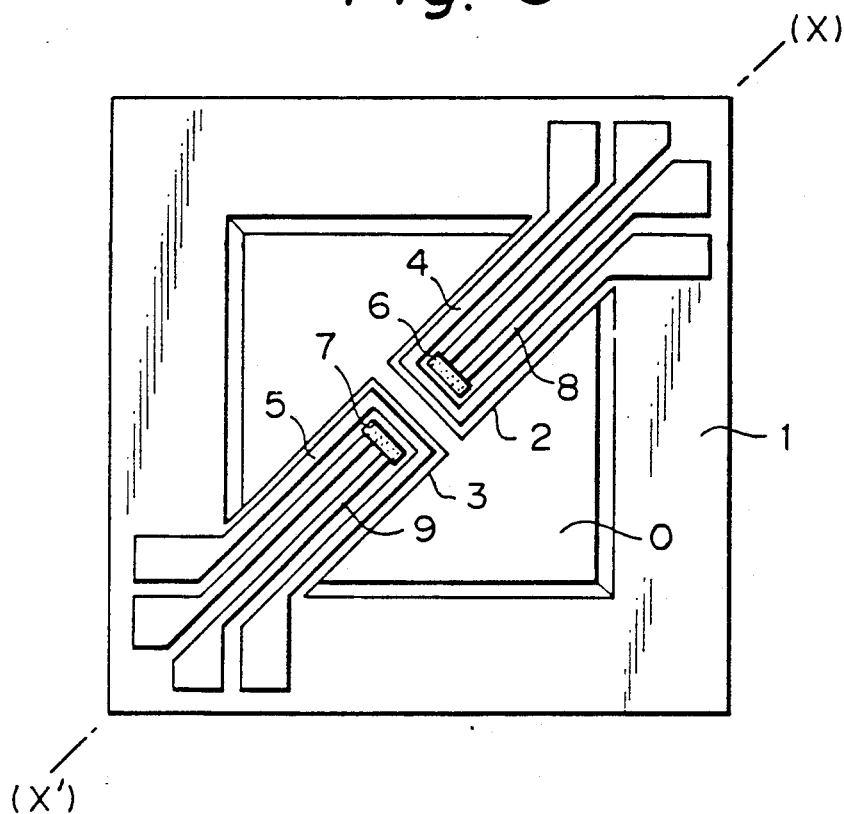
FIG. 3 is a plan view of another example of the gas detecting device in accordance with the present invention.
Figure 4:
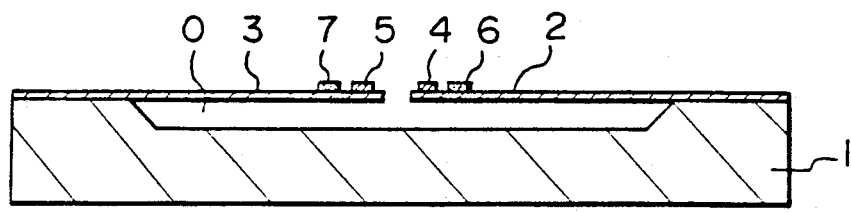
FIG. 4 is a sectional view of the gas detecting device of FIG. 3 taken along the line X—X' in FIG. 3.

FIGS. 3 and 4 illustrate another embodiment of the present invention. This embodiment has substantially the same structure as that of FIG. 1 except that each of the overhang portions 2 and 3 is formed as a cantilever structure.

As illustrated in FIGS. 3 and 4, the cantilever overhang portions 2 and 3 are disposed in a space above the recess 0 undercut by etching the substrate 1. The two cantilevers 2 and 3 are arranged on a diagonal of the square recess 0 aligned with each other, each cantilever extending to the center portion of the recess 0. The constructions of the two cantilever overhangs 2 and 3 are the same except the metal to oxygen composition ratio of the metallic oxide semiconductor films 6 and 7 each of which constitutes a gas sensitive element disposed on a free end of each cantilever. Two detecting leads 8 are connected to the gas sensitive element 6 as well as that two detecting leads 9 are connected to the other gas sensitive element 7. The gas sensitive element (metallic oxide semiconductor film) 6 is surrounded by a heater lead 4 to heat the element 6. Also, the gas sensitive element 7 is surrounded by a heater lead 5 to heat the element 7.

Various known film producing methods such as a sputtering method or a vacuum evaporation method can be used for growing a film on the substrate to form the metallic oxide semiconductor films 6 and 7 thereon. However, it is preferable to form the metallic oxide semiconductor films by using an evaporation apparatus for thin film growth which is proposed by Ohta who is one of the present inventors and which apparatus is disclosed in Japanese Patent Application Laying Open (KOKAI) No. 59-89763.

An example of forming a gas sensitive film using the above-mentioned proposed apparatus is discribed hereinafter. This example of the gas sensitive film is made from tin oxide. Tin oxide is made by evaporating Sn, SnO or $SnO_2$.

More precisely, for example, Sn is chosen as the evaporation source material and held in an evaporator source in a vacuum chamber which is prearranged at a vacuum pressure of an order of $10^{-4}$ Pa. Then, an oxygen gas is charged in the vacuum chamber. The pressure in the chamber is maintained at about 0.1 Pa. In this condition, the apparatus is arranged in such a state that the voltage of the counter electrode is zero, that a voltage of 100 V is applied to the grid and that a power of 400 W is supplied to the filament. A power is supplied to the evaporator source in accordance with a desired film growing speed at which speed the tin oxide film is wished to be formed on the substrate. By supplying the power to the evaporator source, the tin held in the evaporator source is evaporated and a part of the evaporated tin is ionized. The ionized tin firmly combines with oxygen in the chamber so that a tin oxide film is formed on the substrate.

Figure 5:
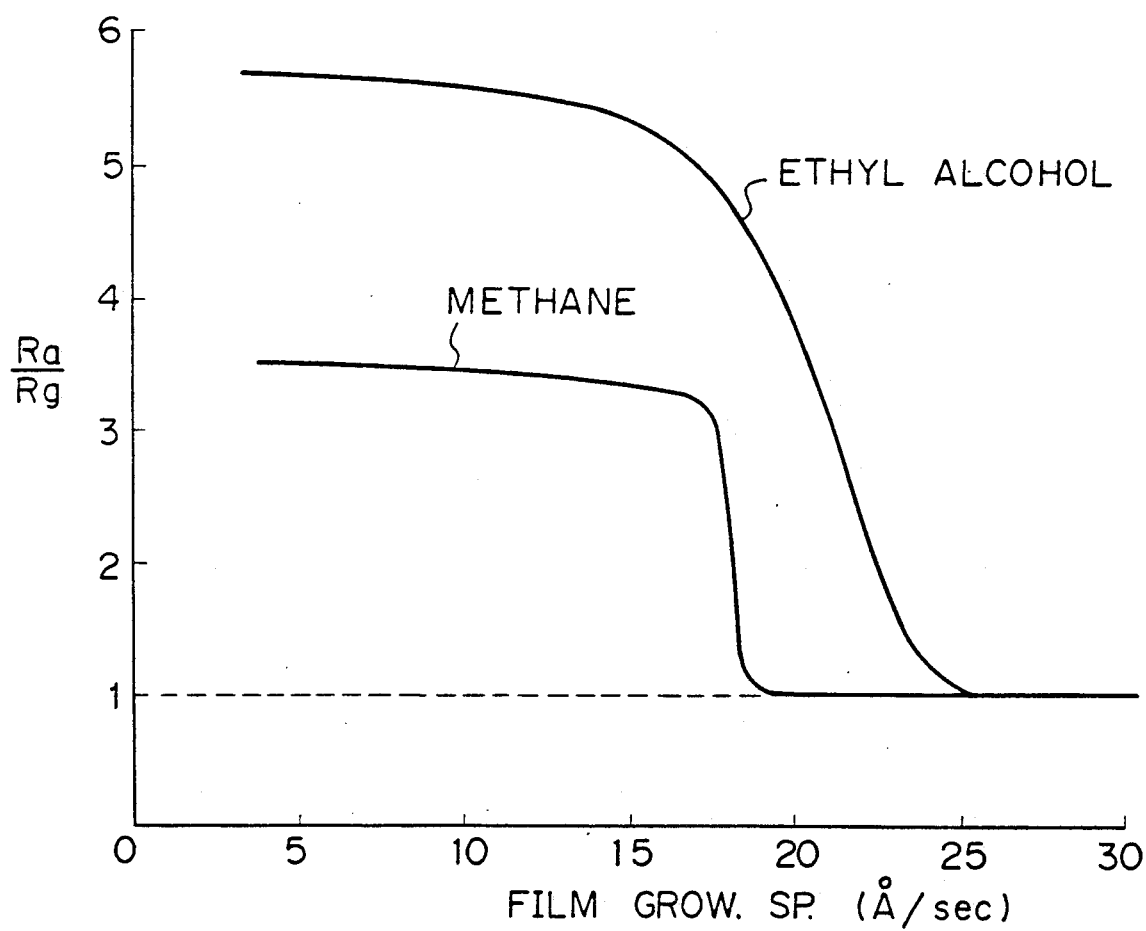
FIG. 5 is a graphical view representing relation between gas sensitivity of the gas sensitive film and the speed of film growth with respect to methane and ethyl alcohol.

FIG. 5 represents a relation between the gas sensitivity and the film growing speed of the metallic oxide film formed by the above-mentioned method with respect to methane and ethyl alcohol.

The gas density of methane with respect to air is 3000 ppm and that of ethyl alcohol is 1000 ppm. The temperature of the gas sensitive film is 450 degrees centigrade. In the graph, Ra represents resistance value of the gas sensitive film in the air atmosphere and Rg represents resistance value in the gas atmosphere. As can be seen from the graph, the gas sensitivity represented by Ra/Rg changes in accordance with the film growing speed at which the gas sensitive film was made. Also, the value Ra/Rg similarly changes in accordance with the change of the gas density.

A method for selectively detecting methane or ethyl alcohol is described below.

With regard to the structure of FIGS. 1 to 4, the first gas sensitive film 6 is formed for example at a film growing speed of 10 Å/sec, while the second gas sensitive film 7 is formed at a film growing speed of 20 Å/sec. As can be seen from FIG. 5, the first gas sensitive film 6 which is formed at a speed of 10 Å/sec is sensitive to either of methane and ethyl alcohol, while the second gas sensitive film 7 which is formed at a speed of 20 Å/sec is sensitive only to ethyl alcohol. In other words, the resistance of the first gas sensitive film 6 changes when either methane or ethyl alcohol is added to the atmosphere, while the resistance of the second gas sensitive film 7 changes only when ethyl alcohol is added to the atmosphere. Therefore, when both of the first and second gas sensitive films 6 and 7 change the resistance thereof, it can be judged that ethyl alcohol exists in the atmosphere, while when only the first gas sensitive film 6 changes the resistance thereof, it can be judged that only methane exists in the atmosphere.

In the above-mentioned embodiments of the present invention, the film growing speed of the tin oxide film is changed to change the composition ratio of tin and to oxygen included in the tin oxide compound. In this case, ratio of tin to oxygen rises according as the film growing speed is heightened.

In order to change the composition ratio of tin to oxygen of the tin oxide compound, it is possible to change the evaporation source material instead of changing the film growing speed of the tin oxide film as mentioned above. For example, Sn is used as the evaporation source material for making the first gas sensitive film 6, whereas $SnO_2$ is used for making the second gas sensitive film 7.

Also, the number of the gas sensitive films is not limited to two as in the case of the embodiments mentioned above. It is possible to provide more than two gas sensitive films each of which is made from a same metallic oxide but has a different metal to oxygen composition ratio being changed from that of the others.

Figure 6:
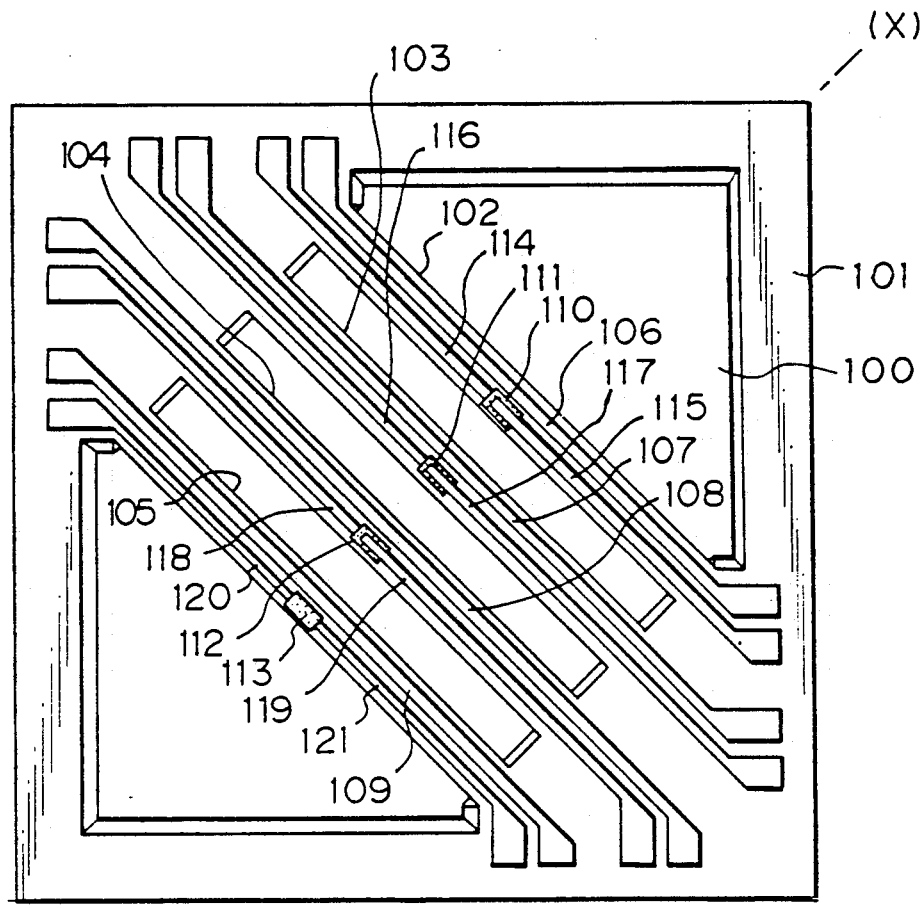
FIG. 6 is a plan view of still another example of the gas detecting device in accordance with the present invention.
Figure 7:
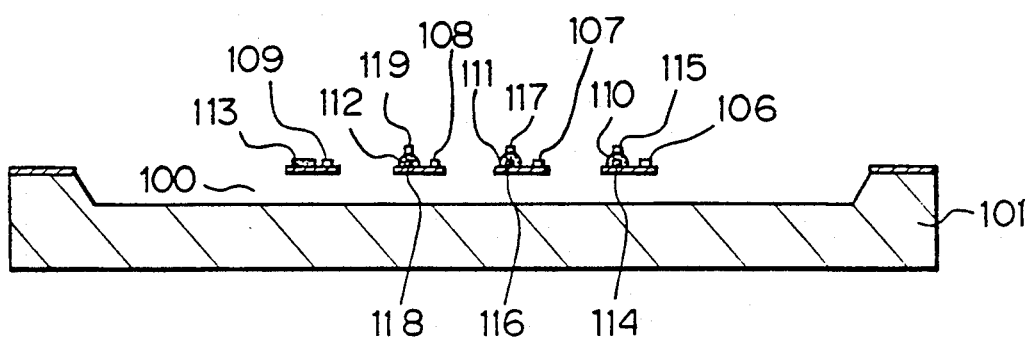
FIG. 7 is a sectional view of the gas detecting device of FIG. 6 taken along the line X—X' in FIG. 6.

FIGS. 6 and 7 represent another embodiment of the gas detecting device in accordance with the present invention which has a bridge-like structure.

This embodiment comprises a substantially square shaped substrate 101 having a substantially square shaped recess 100 undercut by etching in the central portion thereof. Four overhang portions 102, 103, 104 and 105 are disposed over the recess 100. The overhang portions are made from an electric insulation material. The four overhang portions 102, 103, 104 and 105 are disposed side by side in parallel to each other along the diagonal of the recess 100 in a space above the recess 100, each portion being supported at both ends thereof by the edge of the recess 100, forming a bridge-like structure.

The number of the overhang portions is not limited to four. Any plurality of the overhang portions may be disposed on the substrate 101.

Figure 8:
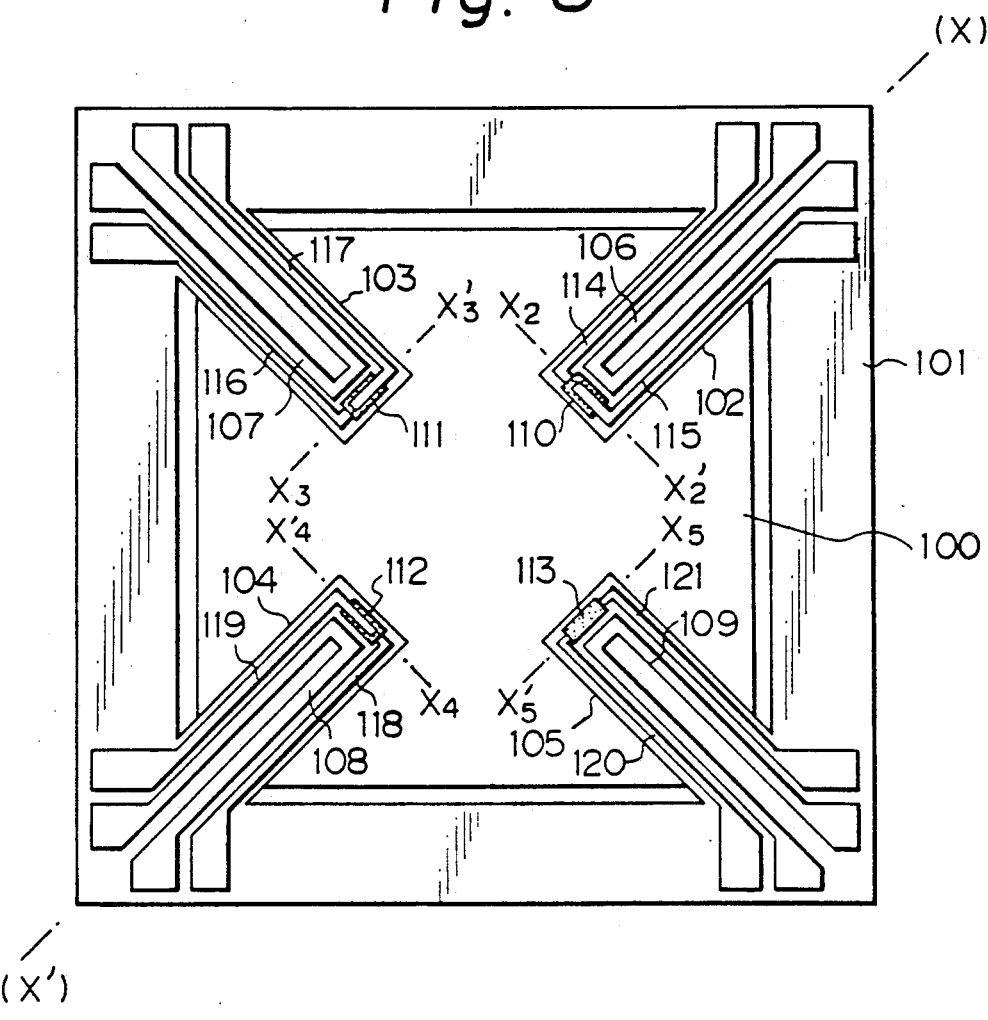
FIG. 8 is a plan view of still another example of the gas detecting device in accordance with the present invention.
Figure 9:
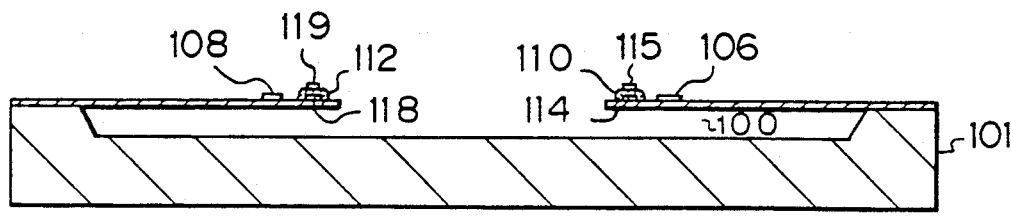
FIG. 9 is a sectional view of the gas detecting device of FIG. 8 taken along the line X—X' in FIG. 8.

FIG. 8 illustrates still another embodiment of the present invention which has a cantilever overhang structure. This embodiment comprises four cantilever overhang portions 102, 103, 104 and 105. However, also the number of the cantilevers of the embodiment is not limited to four. This embodiment of the cantilever structure is described further in detail later. FIG. 9 is a sectional view of the cantilever structure of FIG. 8 taken along the line X—X' in FIG. 8.

The substrate 101 is made from a material which is not deformed at a high temperature and can be easily undercut by etching. Examples of such a material are silicon (Si), aluminium (Al), copper (Cu), nickel (Ni), chromium (Cr), etc. It is desirable to use Si (100) of the above-mentioned examples as the substrate material since the surface (100) of the material is adequate to be etched with the use of a known anisotropy etching solution. Preferably, the substrate 101 has a size of 1 to 4 mm square and 0.1 to 1 mm thick.

The four overhang portions 102, 103, 104 and 105 are formed by etching the substrate 101 to undercut it. On each of the overhang portions 102, 103, 104 and 105 are disposed a heater lead 106, 107, 108, 109, each spanning along the longitudinal bridge. Also, on each overhang portion are disposed a metallic oxide semiconductor film 110, 111, 112, 113 and a pair of detecting electrode leads 114, 115; 116, 117; 118, 119; 120, 121, respectively.

FIGS. 8 and 9 illustrate another embodiment of the present invention. This embodiment has substantially the same structure as that of FIG. 6 except that each of the overhang portions 102, 103, 104 and 105 is formed as a cantilever structure.

Figures 10A, 10B, 10C, 10D:
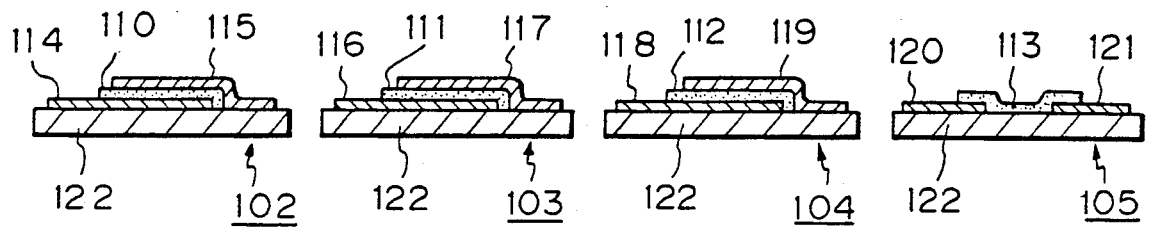
FIG. 10a is a sectional view of the gas detecting device of FIG. 8 taken along the line $X_2$—$X_2'$ in FIG. 8.
FIG. 10b is a sectional view of the gas detecting device of FIG. 8 taken along the line $X_3$—$X_3'$ in FIG. 8.
FIG. 10c is a sectional view of the gas detecting device of FIG. 8 taken along the line $X_4$—$X_4'$ in FIG. 8.
FIG. 10d is a sectional view of the gas detecting device of FIG. 8 taken along the line $X_5$—$X_5'$ in FIG. 8.

As illustrated in FIGS. 8 and 9, the cantilever overhang portions 102, 103, 104 and 105 are disposed in a space above the recess 100 undercut by etching the substrate 101. The four cantilevers 102, 103, 104 and 105 are arranged on the two diagonals of the square recess 100 extending from each corner of the recess, each cantilever extending to the center portion of the recess 100. Each of the metallic oxide semiconductor films constitutes a gas sensitive element disposed on a free end of each cantilever. A pair of detecting electrode leads 114 and 115 are connected to the gas sensitive element 110 mounted on the cantilever overhang portion 102. A heater lead 106 is disposed adjacent to the gas sensitive element (metallic oxide semiconductor film) 110 to heat the element. The other cantilever overhang portions 103, 104 and 105 have substantially the same structure as that of the cantilever 102 mentioned above except that the both electrodes 120 and 121 of the overhang 105 are connected to the lower side of the gas sensitive element 113 (see FIG. 10d), whereas with respect to the other overhangs 102, 103 and 104, one of the pair of electrodes is connected to the upper side of the gas sensitive element (see FIGS. 10a to 10c).

With respect to the gas detecting device illustrated in FIG. 8, the metallic oxide semiconductor films 110, 111 and 112 mounted on the cantilever overhang portions 102, 103 and 104, respectively, are made for example from $TiO_2$ while the metallic oxide semiconductor film 113 mounted on the cantilever overhang portion 105 is made for example from $SnO_2$. This embodiment of the invention is described further in detail with reference to FIGS. 10a to 10d which are sectional views of the structure of FIG. 8 taken along the lines $X_2$—$X_2'$, $X_3$—$X_3'$, $X_4$—$X_4'$ and $X_5$—$X_5'$, respectively.

The gas detecting portion (gas sensitive element) of each of the cantilevers 102, 103 and 104 is constituted by a diode of $Pd/TiO_2$ or $Au/TiO_2$. Each of the detecting electrode leads 115, 117 and 119 made from Pd or Au is connected to the upper side of the $TiO_2$. The thickness of each of the electrode leads 115, 117 and 119 is desirably 200 Å.

The detecting electrode leads 114, 116 and 118 are connected to the lower side of the $TiO_2$ and preferably made from indium (In) in order to come in ohmic contact with $TiO_2$.

The metallic oxide semiconductor film and the electrode lead connected to the film can be formed by any method known per se such as an evaporation method, a sputtering method or a newly proposed method by Ohta who is one of the present inventors using an evaporation apparatus for growing thin film disclosed in Japanese Patent Application Laying Open (KOKAI) No. 59-89763.

Figure 11:
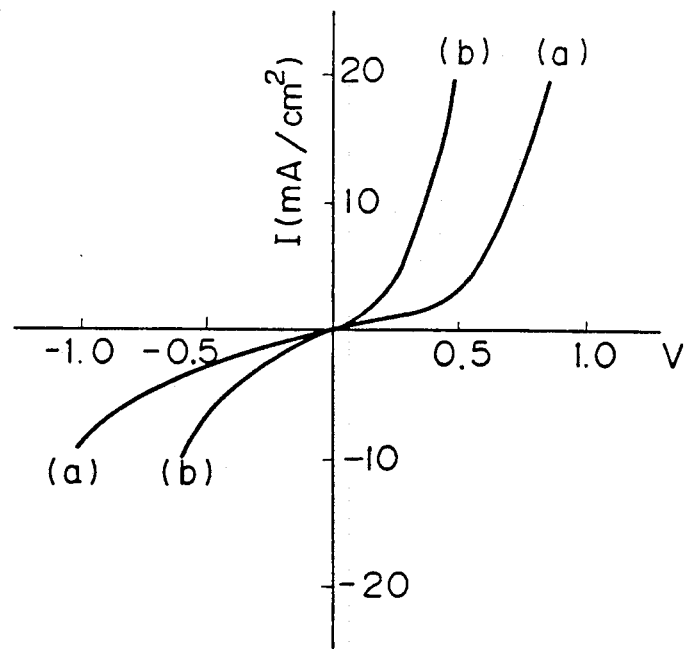
FIG. 11 is a graphical view representing the I-V characteristic of $Pd/TiO_2$ diode.

FIG. 11 illustrates an I-V characteristic of the $Pd/TiO_2$ diode on the condition that the gas detecting portion is heated to a temperature of about 70° C. by the heater lead. In the graph, the line (a) represents a characteristic on the condition that the atmosphere does not contain CO gas. Whereas the line (b) represents a characteristic on the condition that the atmosphere contains CO gas of about 3500 ppm.

By applying a constant forward voltage to the diode, the existence of CO gas can be detected from the change of the current value. The kind of the gas to be detected can be selected by changing the electrode material or temperature of the gas detecting portion.

With respect to the remaining overhang portion 105 which has $SiO_2$ mounted thereon as the gas sensitive element, the gas is detected from the change of the resistance value of the $SiO_2$ itself. In this case, the electrode is made from a material having heat resistance properties such as Pt, Au and Pd.

As an example of the composition of the gas detecting portion, as illustrated in FIGS. 10a to 10d, the gas sensitive films 110, 111 and 112 are made from for example $TiO_2$ while the remaining gas sensitive film 113 is made from $SnO_2$ and the lower electrode leads 114, 116 and 118 are made from indium (In), the upper electrodes 115 and 119 are made from palladium (Pd), the upper electrode 117 is made from gold (Au) and the electrodes 120 and 121 of the overhang 105 are made from platinum (Pt).

The gases which can be detected by the above-mentioned gas sensitive films are represented in the following table 1.

TABLE 1

| Gas Detect. Element | Temp. of Gas Detect. Portion | | |
|---|---|---|---|
| | Room Tem | 70° C. | 350° C. |
| $Pd/TiO_2$ | $H_2$, $SiH_4$ | $H_2$, $SiH_4$, CO | — |
| $Au/TiO_2$ | $SiH_4$ | $H_2$, $SiH_4$ | — |
| $SnO_2$ | X | X | $H_2$, CO, $C_2H_5OH$ |

Note 1: Mark "—" means unusable since temperature is higher than melting point of indium.

Table-2 represents response of the gas sensitive elements mounted on the overhang portions 102, 103, 104 and 105, respectively, with respect to gases of $SiH_4$, $H_2$, CO and $C_2H_5OH$ on the condition that the temperature of the overhangs 102 and 103 is the room temperature, the temperature of the overhang 104 is 70° C. and the temperature of the overhang 105 is 350° C.

In the table-2, mark "O" means that the element responded to the gas, while mark "X" means no response obtained from the element with respect to the gas.

In accordance with the result of the response to the gases as represented in table-2, it is possible to discriminate the gas on the basis of the result of the response of the gas sensitive elements mounted on the overhang portions of the gas detecting device in accordance with the present invention.

TABLE 2

| Gas | Ref No. of Overhang | | | |
|---|---|---|---|---|
| | 102 | 103 | 104 | 105 |
| $SiH_4$ | O | O | O | X |
| $H_2$ | O | X | O | O |
| CO | X | X | O | O |
| $C_2H_5OH$ | X | X | X | O |

The above-mentioned embodiments of FIGS. 6 to 10 comprise tin oxide and titanium oxide for using as the gas sensitive metallic oxide semiconductor. However, the present invention is not limited to the oxide of tin and titanium. It is possible to use the oxide of zinc, indium, nickel, iron, tungsten, cadmium and vanadium.

In accordance with the gas detecting device of the present invention, it is possible to discriminate various kind of other gases by changing the metallic oxide semiconductor and the material of the upper and lower electrode leads and further changing the temperature of the gas detecting portion.

Many widely different embodiments of the present invention may be constructed without departing from the spirit and scope of the present invention. It should be understood that the present invention is not limited to the specific embodiments described in the specification, except as defined in the appended claims.

What is claimed is:

1. A gas detecting device, comprising:
a substrate;

a plurality of overhang portions made from an electric insulation material and disposed in a space over said substrate;

a gas sensitive film made from a metallic oxide semiconductor material and mounted on each of said overhang portions;

said metallic oxide semiconductor material of said gas sensitive film on at least one of said plurality of overhang portions having a composition ratio of metal to oxygen different from that of the other gas sensitive films;

a pair of detecting leads connected to said gas sensitive film; and a heating means for heating said gas sensitive film and mounted on each of said overhang portions.

2. A gas detecting device according to claim 1, wherein said overhang portion is formed as a bridge-like structure supported at both ends thereof on said substrate.

3. A gas detecting device according to claim 1, wherein said overhang portion is formed as a cantilever structure supported at one end thereof by said substrate and has a free end at the other end thereof.

4. A gas detecting device according to claim 1, wherein said substrate has an undercut recess over which said overhang portions are disposed.

5. A gas detecting device according to claim 4, wherein said recess has a substantially square shape and said overhang portion is disposed along a diagonal of said recess.

6. A gas detecting device according to claim 1, wherein said detecting lead is disposed on said overhang portion along a longitudinal direction thereof.

7. A gas detecting device according to claim 1, wherein said heating means is comprised of a heater lead made from an electric resistant material and disposed on said overhang portion in parallel with said detecting lead.

8. A gas detecting device according to claim 1, wherein said substrate is made from Si (100).

9. A gas detecting device according to claim 1, wherein said metal of said metallic oxide semiconductor is an element selected from the group consisting of tin, zinc, iron, titanium, indium, nickel, tungsten, cadmium and vanadium.

10. A gas detecting device according to claim 1, wherein said metallic oxide semiconductor is formed on said substrate by evaporating a metallic material held by an evaporator source in a vacuum chamber by applying an electric voltage thereto and compounding with oxygen in the chamber.

11. A gas detecting device according to claim 10, wherein said composition ratio of metal to oxygen of said metallic oxide semiconductor is changed by changing a film growing speed of said metallic oxide semiconductor.

12. A gas detecting device according to claim 10, wherein said composition ratio of metal to oxygen of said metallic oxide semiconductor is changed by changing said metallic material held by said evaporator source.

13. A gas detecting device, comprising:

a substrate;

a plurality of overhang portions made from an electric insulation material and disposed in a space over said substrate;

a gas sensitive film made from a metallic oxide semiconductor material and mounted on each of said overhang portions;

a pair of detecting leads connected to said gas sensitive film;

said gas sensitive film and detecting leads on at least one of said plurality of overhang portions being made from materials different from those of the other overhang portions; and a heating means for heating said gas sensitive film and mounted on each of said overhang portions.

14. A gas detecting device according to claim 13, wherein the device comprises a means for changing temperature of a detecting portion of at least one of said overhang portions to become different from temperature of the other detecting portions.

15. A gas detecting device according to claim 13, wherein said overhang portion is formed as a bridge-like structure supported at both ends thereof on said substrate.

16. A gas detecting device according to claim 13, wherein said overhang portion is formed as a cantilever structure supported at one end thereof by said substrate and has a free end at the other end thereof.

17. A gas detecting device according to claim 13, wherein said substrate has an undercut recess over which said overhang portions are disposed.

18. A gas detecting device according to claim 17, wherein said recess has a substantially square shape and said overhang portion is disposed along a diagonal of said recess.

19. A gas detecting device according to claim 13, wherein said detecting lead is disposed on said overhang portion along a longitudinal direction thereof.

20. A gas detecting device according to claim 13, wherein said heating means is comprised of a heater lead made from an electric resistant material and disposed on said overhang portion in parallel with said detecting lead.

21. A gas detecting device according to claim 13, wherein said substrate is made from Si (100).

22. A gas detecting device according to claim 13, wherein said metal of said metallic oxide semiconductor is an element selected from the group consisting of tin, zinc, iron, titanium, indium, nickel, tungsten, cadmium and vanadium.

* * * * *